United States Patent [19]

Miwa et al.

[11] Patent Number: 5,714,476
[45] Date of Patent: *Feb. 3, 1998

[54] PROCESS FOR PREPARING COMPOSITIONS CONTAINING NEOTREHALOSE

[75] Inventors: Yoshikatsu Miwa; Takashi Shibuya; Hiroto Chaen, all of Okayama, Japan

[73] Assignee: Kabushiki Kaisha Hayashibara Seibutsu Kagaku Kenkyujo, Okayama, Japan

[*] Notice: The term of this patent shall not extend beyond the expiration date of Pat. No. 5,403,727.

[21] Appl. No.: 315,344

[22] Filed: Sep. 30, 1994

Related U.S. Application Data

[63] Continuation of Ser. No. 236,017, May 2, 1994, Pat. No. 5,403,727, which is a continuation of Ser. No. 791,684, Nov. 14, 1991, abandoned.

[30] Foreign Application Priority Data

Nov. 15, 1990 [JP] Japan ................................ 2-307054

[51] Int. Cl.$^6$ ...................... A61K 31/715; C12P 19/12; A23G 3/00
[52] U.S. Cl. .......................... 514/53; 435/100; 426/658
[58] Field of Search ............................ 435/100; 514/53; 426/658

[56] References Cited

U.S. PATENT DOCUMENTS 5,403,727  4/1995  Miwa et al. ............................ 435/100

FOREIGN PATENT DOCUMENTS 480640      4/1992   European Pat. Off. .
50-154485  12/1975   Japan .
257888     10/1990   Japan .

OTHER PUBLICATIONS

Chemical Abstracts 110(9): 74133g (1989) (Kobayashi et al).

Haworth et al., *J. Chem. Society*, 2847–2850 (1931).

Bradling et al., *Carb. Res.*, 126, 125–156, (1984).

Paulson et al., *J. Biol. Chem.*, 253(16), 5617–5624 (1978).

Sharp et al., *J. Chem. Society*, 258–288 (1951).

Onishi et al., *Chemical Abstracts*, 76(21),CA127294y (1970).

Kobayashi et al; *Foods containing trehalose with good anticaries and Bifidobacterium growth–promoting activities*; Chemical Abstracts; vol. 110; No. 74134; p. 525; Oct. 6, 1988.

Kobayashi et al; *Enzymatic manufacture of neotrehalose and centose*; Chemical Abstracts; vol. 110; No. 152832; p. 593; Sep. 8, 1988.

Ajisaka et al; *Regioselective syntheses of trehalose–containing trisaccharides using various glycohydrolases*; Carbohydrate Research; vol. 199; pp. 227–234; 1990.

*Primary Examiner*—Michael G. Wityshyn
*Assistant Examiner*—Francisco C. Prats
*Attorney, Agent, or Firm*—Browdy and Neimark

[57] ABSTRACT

Neotrehalose is prepared in a relatively high-yield by a process comprising allowing β-galactosidase to act on a solution containing lactoneotrehalose to form neotrehalose and recovering the resultant neotrehalose. The neotrehalose is a non-reducing oligosaccharide having a satisfiable stability and a rich- and high-quality-sweetness and is assimilated and utilized as energy source in vivo when orally administered. Neotrehalose in the form of crystal has a satisfiable handleability because it is readily soluble in water and substantially free of hygroscopicity. These render neotrehalose very useful in the fields of food-, cosmetic- and pharmaceutical-industries.

14 Claims, 5 Drawing Sheets

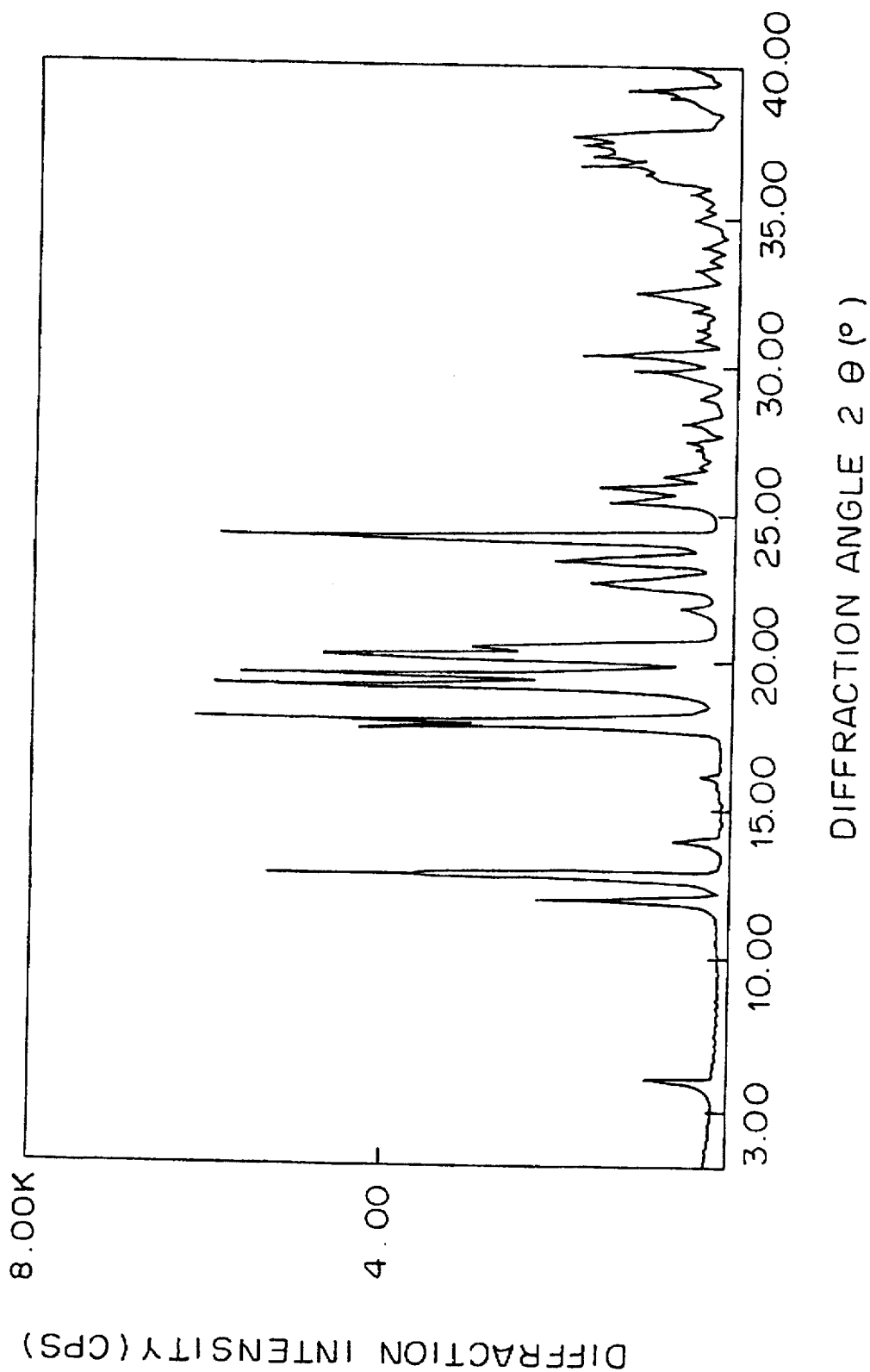

PROCESS FOR PREPARING COMPOSITIONS CONTAINING NEOTREHALOSE

This is a continuation of parent application Ser. No. 08/236,017 filed May 2, 1994, now U.S. Pat. No. 5,403,727, which itself is a continuation of application Ser. No. 07/791,684 filed Nov. 14, 1991, now abandoned.

BACKGROUND OF THE INVENTION

1. Field of the Invention

The present invention relates to a process for preparing neotrehalose and its uses, more particularly, it relates to a preparation of neotrehalose comprising allowing β-galactosidase (EC 3.2.1.23) to act on an aqueous solution containing lactoneotrehalose and recovering the resultant neotrehalose, as well as to orally-administrable products containing said neotrehalose.

2. Description of the Prior Art

Neotrehalose, which is a disaccharide shown by the formula O-α-D-glucopyranosyl β-D-glucopyranoside or O-β-D-glucopyranosyl α-D-glucopyranoside, is a well known compound. Neotrehalose has a sweetness, non-reducibility, satisfiable stability, and high water-solubility, and these merits render neotrehalose very useful in the preparations of orally-administrable products, for example, foods, beverages, cigarettes and tobaccos.

Although methods to prepare neotrehalose, for example, those using chemical syntheses as reported in W. N. Haworth et al., *Journal of the Chemical Society*, pp.2847–2850 (1931), and in V. E. S. Sharp et al., ibid, pp.285–288 (1951), have been known, the yield of neotrehalose is extremely low and there exist many problems which should be overcome in view of the safeness, prior to actual use.

The preparations of neotrehalose from natural substances with a greater safety or those by using biochemical syntheses have been proposed. For example, K. Matsuda reported in *Journal of the Agricultural Chemical Society of Japan*, Vol.30, No.2, pp.119–123 (1959) that a small amount of neotrehalose was present in a koji extract together with isomaltose and kojibiose: In this report, neotrehalose was prepared by a method comprising subjecting a koji extract to a column chromatography using activated charcoal to remove non-fermenting saccharides in the extract, recovering fractions containing disaccharides, treating the disaccharides with phenylhydrazine, separating the resultant sediment to obtain a filtrate, acetylating the saccharides in the filtrate to form crystalline octaacetates of the disaccharides, and deacetylating the crystalline octaacetates. S. Kobayashi et al. disclosed in Japanese Patent Laid-Open No. 216,492/88 a method containing a step of allowing a cyclodextrin-forming enzyme to act on amylaceous substance to form neotrehalose together with centose: In this report, high-performance liquid chromatography (HPLC) revealed that the reaction solution contained 18.6% neotrehalose and 20.0% centose, and paper chromatography analysis revealed that the resultant neotrehalose-rich fraction contained about 20% of nigerose, kojibiose and isomaltose. S. Kobayahshi et al. also proposed a method to prepare neotrehalose from the reaction solution comprising heating the reaction solution to inactivate the remaining cyclodextrin-forming enzyme, adding to the resultant solution glucoamylase and yeast at the same time to digest and remove the forming glucose, removing the remaining yeast, autoclaving the resultant after the addition of sodium hydroxide, neutralizing the resultant product, and recovering the resultant neotrehalose with column chromatography and/or the sedimentation method using solvents. None of the methods has as yet been industrially carried out because of the following reasons: (i) The methods only produce neotrehalose preparations with a relatively low-content of neotrehalose; and (ii) The purification steps required after the methods are extremely complicated, and the yield of neotrehalose attained thereby is relatively low.

SUMMARY OF THE INVENTION

There has been a great demand for a preparation of neotrehalose and its uses, wherein said neotrehalose is used with a high-safeness and readily prepared in a relatively-high yield.

The present inventors have studied preparations of neotrehalose by using biochemical syntheses.

As a result, the present inventors discovered that neotrehalose was readily formed in a relatively-high yield by allowing β-galactosidase (EC 3.2.1.23) to act on lactoneotrehalose, as material, shown by the formula O-β-D-galactopyranosyl-(1→4)-O-β-D-glucopyranosyl α-D-glucopyranoside which had been applied by the present inventors to Japanese Patent Office as Application No. 268,677/90. Thus, the present inventors accomplished the present invention. The present inventors also found that neotrehalose was a saccharide which was readily digestible in vivo based on the result of in vivo test with a high-purity neotrehalose according to the present invention, and accomplished its uses, i.e. orally-administrable products containing neotrehalose.

BRIEF DESCRIPTION OF THE ACCOMPANYING DRAWINGS

FIG. 3 shows a powder x-ray diffraction pattern of a crystalline lactoneotrehalose specimen.

DETAILED DESCRIPTION OF THE INVENTION

Figure 1:
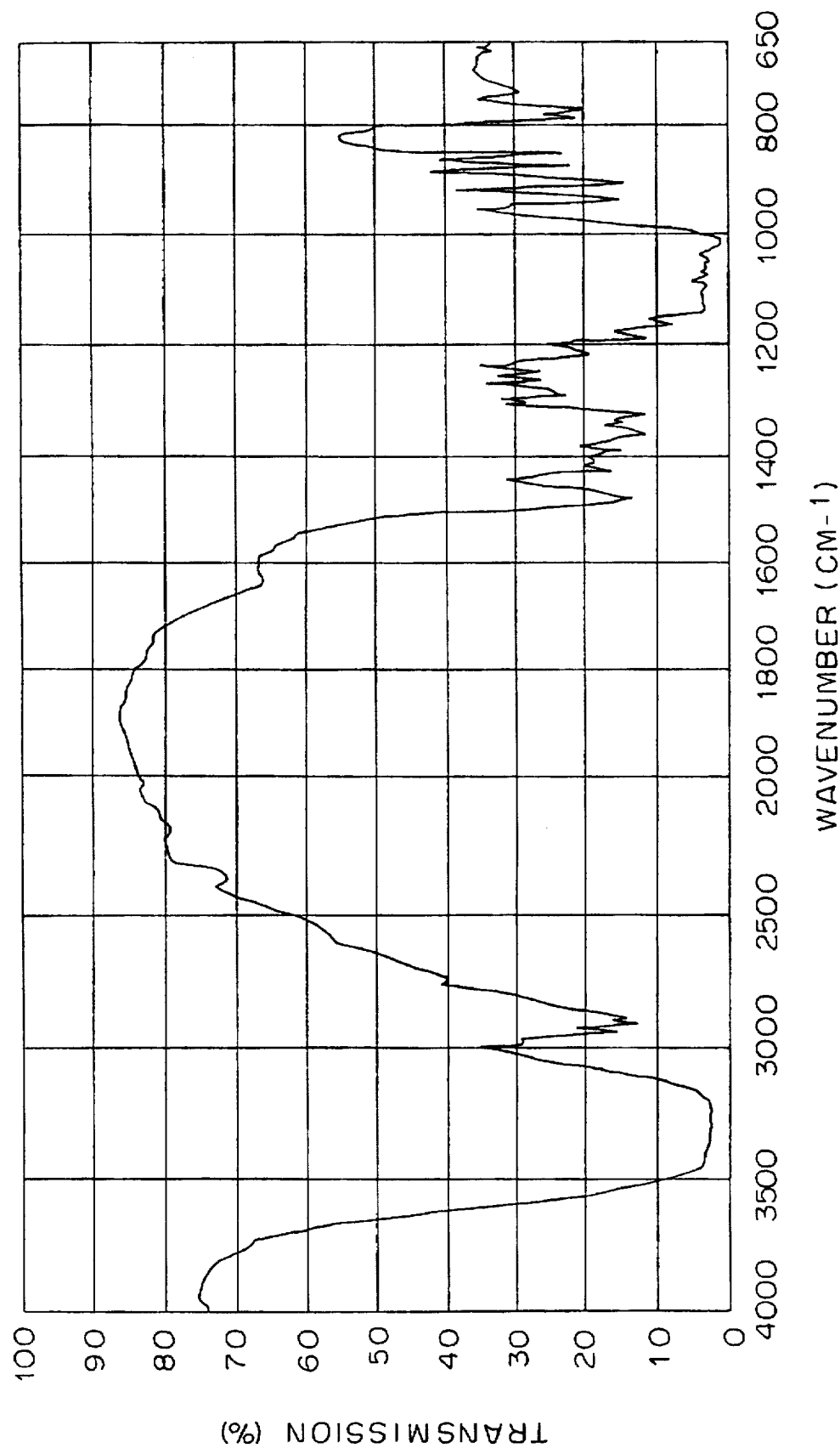
FIG. 1 shows an infrared absorption spectrum of a crystalline lactoneotrehalose specimen.

The present invention relates to a preparation of neotrehalose and its uses, more particularly, it relates to a preparation of neotrehalose comprising allowing β-galactosidase (EC 3.2.1.23) to act on an aqueous solution containing lactoneotrehalose and recovering the resultant neotrehalose, as well as to orally-administrable products containing said neotrehalose.

Lactoneotrehalose, as material, usable in the invention will be described.

Although lactoneotrehalose may be formed through chemical syntheses, much more preferable an industrial view point, biochemical processes wherein lactoneotrehalose is advantageously formed by allowing a saccharide-transferring enzyme to act on amylaceous an aqueous solution containing lactose and amylaceous substance.

Commercially-available lactoses can be used in the invention. If necessary, crude lactose preparations such as milk and milk serum wherein lactose is present can be used in the invention.

The amylaceous substances advantageously usable in the invention are, for example, gelatinized starch, liquefied starch, solubilized starch, partial starch hydrolysate, and saccharide-transferred amylaceous products.

Although the saccharide-transferring enzyme most preferable in the invention is cyclomaltodextrin glucanotransferase (EC 2.4.1.19), α-glucosidase (EC 3.2.1.20) can be also used in the invention.

In the case of using cyclomaltodextrin glucanotransferase, those derived from microorganisms of the genera Bacillus and Klebsiella can be advantageously used.

The α-glucosidases usable in the invention are, for example, those derived from microorganisms of the genera Penicillium and Mucor.

Although any saccharide-transferring reaction can be used in the invention, as long as lactoneotrehalose is formed by the reaction, and usually, lactoneotrehalose is formed by allowing either cyclomaltodextrin glucanotransferase or α-glucosidase to act on an aqueous solution containing lactose and amylaceous substance such as partial starch hydrolysate to transfer the α-glucosyl residue of the amylaceous substance to the glucosyl residue of lactose.

Among these saccharide-transferring reactions, the method using cyclomaltodextrin glucanotransferase is generally most favorable because it can attain a higher lactoneotrehalose yield with cheaper amylaceous substances as saccharide donor. In particular, the use of cyclomaltodextrin glucanotransferase derived from *Bacillus stearothermophilus* is extremely favorable from industrial view point because the cyclomaltodextrin glucanotransferase can be allowed to act on substrate at a relatively-high temperature, and this inhibits the retrogradation of amylaceous substance in a reaction solution and the contamination of microorganisms, as well as facilitating the saccharide-transferring reaction.

In this case, one or more units/g amylaceous substance, preferably, 10–1,000 units/g amylaceous substance of cyclomaltodextrin glucanotransferase is allowed to act on an aqueous solution containing lactose together with amylaceous substance such as gelatinized starch, liquefied starch, amylodextrin, cyclodextrin and partial starch hydrolysate having a dextrose equivalent (DE) of about 1–50, for about 1–100 hours, preferably, for about 4–70 hours, to form lactoneotrehalose together with oligosaccharides, for example, α-glycosyl lactoneotrehalose such as α-glucosyl lactoneotrehalose, α-maltosyl lactoneotrehalose, α-maltotriosyl lactoneotrehalose and α-maltotetraosyl lactoneotrehalose, wherein one or more α-glucosyl residues are bound to lactoneotrehalose. These oligosaccharides are then subjected to glucoamylase to form and accumulate lactoneotrehalose, followed by recovering the accumulated lactoneotrehalose.

Replacement of glucoamylase with β-amylase leads to the formation and accumulation of lactoneotrehalose, α-glucosyl lactoneotrehalose and maltose.

The above saccharide-transferring reactions with or without a hydrolytic reaction form a lactoneotrehalose-containing solution containing usually about 5–40 w/w % (the symbol "w/w %" will hereinafter be abbreviated as "%", if not specified otherwise) of lactoneotrehalose, on the dry solid basis (hereinafter abbreviated as "d.s.b."), which is then filtered and purified into liquid, prior to use: Such a liquid may be concentrated, and if necessary, dried into syrup or solid.

In general, in order to augment the merits of lactoneotrehalose, a solution containing lactoneotrehalose is separated and purified into a high-lactoneotrehalose content product, prior to use. Such separation and purification are achievable, for example, with fermentation using yeast, membrane filtration, fractional-sedimentation, crystallization and/or column chromatography, as long as the concomitant saccharides are removed therewith.

Since lactoneotrehalose is readily crystallizable from the concentrate of the high-lactoneotrehalose content solution, crystalline lactoneotrehalose can be advantageously prepared from the solution, prior to use.

Any method for preparing neotrehalose from a lactoneotrehalose obtained by the above methods can be used in the invention, as long as neotrehalose is formed by allowing β-galactosidase to act on the lactoneotrehalose. β-Galactosidase is allowed to act on lactoneotrehalose by adding β-galactosidase to an aqueous solution containing lactoneotrehalose and allowed to react at a temperature and pH which are usually chosen from 20°–80° C. and 3–9 respectively.

In this case, commercially-available β-galactosidases are appropriately used, and if necessary, β-galactosidases can be advantageously prepared by culturing a microorganism capable of producing β-galactosidase, and recovering β-galactosidase from the cells or the supernatant, prior to use.

Such β-galactosidases can be immobilized for repeated use.

Although the neotrehalose content in the solutions containing neotrehalose thus obtained varies depending on the lactoneotrehalose content in the material, the solutions containing about 10–66% of neotrehalose, d.s.b., can be usually used intact. If necessary, the solutions can be further purified, concentrated and dried, prior to use.

In general, in order to augment the merits of neotrehalose, a solution containing neotrehalose is separated and purified into a high-neotrehalose content product, prior to use. Such separation and purification are achievable, for example, with fermentation using yeast, membrane filtration, fractional-sedimentation, crystalization and/or column chromatography, as long as the concomitant saccharides are removed therewith. In particular, a method wherein column chromatography using strongly-acidic cation exchange resins as disclosed in Japanese Patent Laid-Open Nos. 23,799/83 and 72,598/83 can be used to remove concomitant saccharides and to collect neotrehalose-rich fractions. In this case, either of fixed-bed-, moving-bed- and simulated-moving-bed-methods can be suitably employed.

Since neotrehalose is readily crystallizable from the concentrate of the high-neotrehalose content solution, crystalline neotrehalose can be advantageously prepared from the solution, prior to use.

The process for preparing crystalline neotrehalose according to the present invention usually contains a step of providing a neotrehalose solution with a saturation degree of about 1.05–4.0, more particularly, a step of preparing a saccharide composition containing 50% or more neotrehalose, d.s.b., into a solution having a concentration of about 50–95%, keeping the solution at a temperature which does not freeze the solution and not exceed the melting point of a neotrehalose crystal, for example, in the range of about 10°–120° C.

The crystallization step usable in the invention contains a step of placing in a crystallizer a supersaturated neotrehalose solution which is kept at a relatively-high temperature, i.e.

40°–100° C., and gradually cooling the solution under gentle-stirring conditions, preferably, in the presence of 0.1–20% seed, to accelerate the crystallization. To collect crystalline neotrehalose from the resultant massecuite, any conventional method is employable, as long as crystalline neotrehalose can be obtained thereby; for example, separation-, block-pulverization-, fluidized-bed-granulation- and spray-drying-methods. The separation method is to separate a massecuite into crystalline neotrehalose and the mother liquor (molasses) using a basket-type centrifuge. If necessary, the resultant crystalline neotrehalose can be readily washed by spraying thereto a small amount of cool water. Thus, the separation method can be advantageously used to prepare a higher purity of crystalline neotrehalose. Since the other three methods do not remove molasses, they do not improve the purity of neotrehalose in the resultant massecuite, but realize a high-product yield. Accordingly, the products obtained by the three methods usually contain crystalline neotrehalose together with other saccharide components. The saccharide components vary dependently on the enzymatic reaction used: For example, the components contains neotrehalose along with galactose and glucose.

In the case of the block-pulverization method, a massecuite having a concentration of 85–95% and a crystallinity of about 10–60% is usually allowed to stand for about 0.5–5 days so that the whole content is crystallized and solidified into blocks which are then pulverized by scraping or cutting into a reduced-hygroscopic crystalline powder containing molasses.

In the case of the spray-drying method, a massecuite having a concentration of 65–80% and a crystallinity of about 20–40% is usually spray-dried in the ventilation of a hot air, for example, 60°–100° C. air which does not melt crystalline neotrehalose, and then aged for about 1–20 hours in the ventilation of 30°–60° C. air to obtain a reduced-hygroscopic crystalline neotrehalose powder containing molasses.

The physicochemical properties of the powders, such as melting point and specific rotation, vary dependently on the neotrehalose content, d.s.b. Usually, the melting point decreases and widens as the neotrehalose content lowers. The hygroscopicity of the powders increases as the neotrehalose content lowers. Therefore, the neotrehalose content in the powders should be appropriately chosen to meet to their final use.

The neotrehalose according to the present invention is a non-reducing oligosaccharide having an extremely-high stability and rich sweetness. The neotrehalose is metabolized and utilized as energy source when orally administered. The handleability of crystalline neotrehalose is satisfiable because it is readily soluble in water and substantially free of hygroscopicity. Since dental-caries-inducing microorganisms only metabolize the neotrehalose at a relatively-low level, it can be used as a sweetener with a reduced dental-caries-inducibility. Since the neotrehalose is a sweetener with a satisfiable stability, it can be advantageously used as a sugar-coating agent for tablet in combination with a binder such as pullulan and hydroxyethyl starch. The neotrehalose has a good chemical stability, as well as other properties such as osmosis-pressure controlling ability, filler-imparting ability, gloss-imparting ability, moisture-retaining ability, viscosity-imparting ability, decreased fermentability, and crystalization-preventing ability for other saccharides.

These merits render the neotrehalose very useful in the preparations of orally-administrable products, for example, foods, beverages, cigarettes, tobaccos, feeds and pet foods, as well as in the preparations of cosmetics and pharmaceuticals.

The present neotrehalose can be used as a seasoning without further treatment to impart sweetness. If necessary, the neotrehalose can be used in combination with an adequate amount of one or more other sweeteners, for example, starch sugar powder, glucose, maltose, sucrose, isomerized sugar, honey, maple sugar, sorbitol, dihydrochalcone, stevioside, α-glycosyl stevioside, rebaudioside, glycyrrhizin, L-aspartyl L-phenylalanine methyl ester, saccharin, glycine and alanine. The present neotrehalose can be mixed with a filler such as dextrin, starch and lactose, prior to use.

The present neotrehalose in the form of powder can be molded solely or after mixing it with filler, vehicle and/or binder into granule, sphere, short-rod, sheet, cube or tablet, prior to use.

The present neotrehalose can be advantageously used in foods and beverages in general to impart to them a sweetness and also to improve their tastes and qualities because the neotrehalose has a relatively-high resistance to acid and heat, as well as having a sweetness which well harmonizes with other substances with sour, salty, bitter, delicious and astringent.

Thus, the present neotrehalose can be advantageously used in foods and beverages in general, for example, seasonings such as soy sauce, say sauce powder, miso, miso powder, "moromi", "hishio", "furikake", mayonnaise, dressing, vinegar, "sanbai-zu", "funmatsu-sushi-su", "chuka-no-moto", "tentsuyu" (soup for tenpura), "mentsuyu" (soup for Japanese-style noodles), Worcester sauce, ketchup, "yakiniku-no-tare" (soup for grilled meat), curry roux, stew premix, soup premix, "dashi-no-moto", mixed seasoning, "mirin" (heavily sweetened sake), "shin-mirin" (synthetic mirin), table sugar and coffee sugar.

The present neotrehalose can be advantageously used in foods and beverages in general to impart to them a sweetness and to improve their tastes and qualities. Examples of such foods and beverages are Japanese-style confectioneries such as "senbei" (rice crackers), "arare" (pellet-shaped senbei), "okoshi" (millet-and rice cracker), rice paste, "manju" (bun with a bean-jam filling), "uiro" (sweet rice jelly), "an" (bean jam), "yokan" (sweet jelly of beans), "mizu-yokan" (soft adzuki-bean jelly), "kingyoku", jelly, castella and "amed-ama" (Japanese-style toffee); Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve and "kaki-gori" (shaved ice); pastes such as flour paste, peanut paste, fruit paste and spread; processed fruits such as jam, marmalade, syrup-preserved fruit and crystallized fruit; processed foods of vegetables; pickled products such as "fukujin-zuke" (sliced vegetables picked in soy sauce), "bettara-zuke" (fresh radish pickles), "senmai-zuke" and "rakkyo-zuke" (pickled shallots); premixes for pickled products such as "takuan-zuke-no-moto" and "hakusai-zuke-no-moto"; meat products such as ham and sausage; fish meat products such as fish meat ham, fish meant sausage, "kamaboko" (boiled fish paste), "chikuwa" (literally bamboo wheels) and "tenpura" (deep-fried foods); relishes such as "uni-no-shiokara" (salted guts of sea urchin), "ika-no-shiokara" (salted guts of squid), "su-konbu", "saki-surume" and "fugu-no-mirinboshi"; "tsukudani" (food boiled down in soy sauce) such as those of "nori" (dried seaweed), "sansai" (mountain vegetables), "surume" (dried squid), small fish and shellfish; daily dishes such as "nimame" (cooked beans), potato salad and "konbu-maki" (tangle roll); egg and milk products;

bottled and canned products such as those of meat, fish meat, fruit and vegetable; alcoholic drinks such as synthetic sake, "zojo-shu", liqueur, wine and whisky; beverages such as coffee, cocoa, juice, carbonated beverage, lactic acid beverage and lactobacillus beverage; and premixes and instant foodstuffs such as pudding premix, hot cake premix, "sokuseki-shiruko" (premix of adzuki-bean soup with rice cake) and instant soup; and foods and beverages such as baby food, beverage supplemented with nutritional ingredients, and food for medical treatment.

The present neotrehalose can be advantageously used in feeds and pet foods for domestic animals and poultries including honey bee, silkworm and pet fish for the improvement of the taste qualities of feeds and pet foods. The present neotrehalose can be advantageously used as a sweetener, taste-improving agent and quality-improving agent in special foods and beverages, cosmetics and pharmaceuticals, for example, cigar, cigarette, dentifrice, lipstick, lip cream, internal medicine, troche, cod-liver oil drop, oral refreshing agent, cachou and gargle in the form of a solid, paste or liquid.

As described above, the wording "orally-administrable products" as referred to in the invention means those which can be orally taken or used, for example, foods, beverages, cigarettes, tobaccos, feeds and pet foods, cosmetics and pharmaceuticals. Any method to incorporate neotrehalose in the orally-administrable products can be used in the invention, as long as neotrehalose is incorporated in the products thereby before completion of their processing. For example, conventional methods such as mixing, kneading, dissolving, melting, soaking, permeating, spreading, applying, coating, spraying, injecting, crystallizing and solidifying are freely chosen.

The lactoneotrehalose as material and the neotrehalose according to the present invention will be explained by Experiments 1 and 2 respectively.

EXPERIMENT 1

Preparation of Lactoneotrehalose and its Physicochemical Properties

Experiments 1-1

Preparation of Lactoneotrehalose

Fifty parts by weight of commercially-available lactose and 50 parts by weight of "PINE-DEX #1", a dextrin product (DE 8) commercialized by Matsutani Chemical Ind., Co., Ltd., Hyogo, Japan, were dissolved in 150 parts by weight of water while heating, and the solution was heated to 60° C., adjusted to pH 6.0, added with 300 units/g dextrin of a cyclomaltodextrin glucanotransferase from *Bacillus stearothermophilus*, commercialized by Hayashibara Biochemical Laboratories Inc., Okayama, Japan, allowed to react for 20 hours, heated at 100° C. for 15 minutes to inactivate the remaining enzyme, cooled to 55° C., adjusted to pH 5.0, added with 15 units/g dextrin of "Glucozyme", a glucoamylase specimen commercialized by Nagase Biochemicals Ltd., Kyoto, Japan, allowed to react for 16 hours, and heated at 100° C. for 15 minutes to inactivate the remaining enzyme. The resultant solution containing about 24% lactoneotrehalose, d.s.b., was decolored with activated charcoal and treated with ion exchange ($H^+$- and $OH^-$-form) for deionization and purification. The solution thus obtained was concentrated to give a concentration of about 45% and subjected to column chromatography, followed by the recovery of lactoneotrehalose-rich fractions. As the fractionating resin was used "Amberlite XT-1016 ($Na^+$-form)", a strongly-acidic cation exchange resin commercialized by Japan Organo Co., Ltd., Tokyo, Japan, which was suspended in water and packed in jacketted-stainless steel columns, inner diameter of 5.4 cm each. Four columns, gel-bed depth of 5 m each, were cascaded to give a total gel-bed depth of about 20 m.

While keeping the inner temperature of the columns at 55° C., 5 v/v % of a material saccharide solution was added thereto, and 55° C. water was passed through the columns at a flow rate of SV 0.3 to effect fractionation, thus obtaining lactoneotrehalose-rich fractions. A portion of lactoneotrehalose-rich fractions, lactoneotrehalose content of about 67%, d.s.b., which had been pooled by the repetition of the above method, was concentrated to give a concentration of 75%, and allowed to stand overnight at 20° C. to effect crystallization. The resultant crystal as seed crystal was added to a high-lactoneotrehalose content solution, which had been prepared by concentrating the lactoneotrehalose-rich fractions to give a concentration of 70%, to effect crystallization under gentle-stirring conditions. The resultant massecuite was separated, and the formed crystal was sprayed with a small amount of water to obtain a high-purity crystalline lactoneotrehalose which was then dissolved in water and treated similarly as above to effect recrystallization. Thus, about 3 parts by weight of a high-purity crystalline lactoneotrehalose, purity of 99.8% or higher was obtained.

Experiment 1-2

Physicochemical Properties of Lactoneotrehalose

The physicochemical properties of lactoneotrehalose were studied with a high-purity crystalline lactoneotrehalose specimen prepared by the method in Experiment 1-1.

(1) Elemental analysis Found; C=42.8%, H=6.4%, O=50.8% Calculated; C=42.86%, H=6.39%, O=50.75% (for chemical formula $C_{18}H_{32}O_{16}$)

(2) Molecular weight 504.4

(3) Melting point 168.5°–169.0° C.

(4) Specific rotation $[\alpha]_D^{20}$=+82.6° (c=2.0, $H_2O$)

(5) uv-Absorption spectrum Exhibiting no characteristic uv-absorption when tested in water.

(6) Infrared absorption spectrum Two mg of the crystal and 200 mg of dried KBr were mixed by stirring to obtain about 0.6 mm thick transparent tablet, and the infrared spectrum of the crystal was determined therewith. The result was shown in FIG. 1.

(7) Solubility 21.7 g of the crystal dissolves in 100 g water at 25° C.

Figure 2:
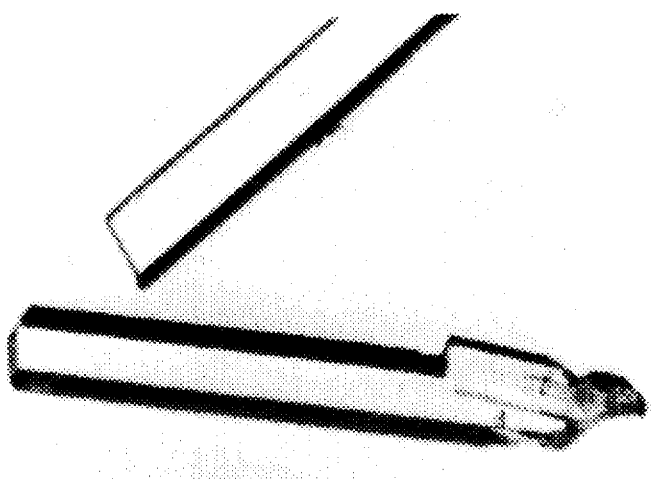
FIG. 2 shows a microscopic photograph (×50) of a crystalline lactoneotrehalose specimen.

(8) Heat of dissolution 20.0 cal/g (9) Physical properties and color Colorless and transparent crystal having a true specific gravity of 1.59. Pulverized crystal has a favorable taste and about ¼ sweetening power of sucrose and exhibits a white appearance, but exhibits no odor. Free of hygroscopicity and deliquescence. The Karl Fischer's method revealed that the moisture content of crystals predried in vacuo at 60° C. for 16 hours is less than 3.0%. FIG. 2 shows a microscopic photograph of a crystal obtained by crystallization in an aqueous solution. An aqueous solution of the crystal shows neutral or slight acidity.

(10) Solubility in solvents Readily soluble in water, 0.1N sodium hydroxide, and 0.1N hydrochloric acid; scarcely soluble in methanol and ethanol; and insoluble chloroform and ethyl acetate.

(11) Coloring reaction Turning green on the anthrone-sulfuric acid reaction. Negative to both the Fehling's reaction and the iodine coloration reaction.

(12) Structure
  (a) Hydrolysis with 1N-sulfuric acid gives 2 moles of D-glucose and one mole of D-galactose.
  (b) Gas chromatographic analysis on saccharides obtained by acetylating the crystal with methylhexytol revealed that the crystal formed one mole of 1,5-di-O-acetyl-2,3,4,6-tetra-O-methylglucitol, one mole of 1,5-di-O-acetyl-2,3,4,6-tetra-O-methylgalactitol, and one mole of 1,4,5-tri-O-acetyl-2,3,6-tri-O-methylglucitol.
  (c) Infrared absorption spectrum of the crystal gives the absorption near at 910 $cm^{-1}$ inherent to β-D-galactopyranosyl bond, the absorption near at 880–875 $cm^-$inherent to β-D-glucopyranosyl bond, and the absorption near at 860–840 $cm^-$inherent to α-D-glucopyranosyl bond.
  (d) When subjected to the action of β-galactosidase, D-galactose and neotrehalose are formed.
  (e) When subjected to the action of β-glucosidase, D-glucose and lactose are formed.
  (f) On carbon-13 nuclear magnetic resonance ($^{13}$C-NMR) analysis, eighteen $^{13}$C signals were observed and all of eighteen carbons of the crystal showed different chemical shifts respectively. Based on the chemical shifts of β-D-galactopyranose, β-D-glucopyranose and α-D-glucopyranose as the standard substances reported in J. H. Bradbury et al., Carbohydrate Research, Vol.126, pp.125–156 (1984), each carbon of the crystal is assigned to reveal that the crystal has the structure of O-β-D-galactopyranosyl-(1→4)-O-β-D-glucopyranosyl α-D-glucopyranoside.

Based on the above results, the chemical structure of the crystal can be shown as follows:

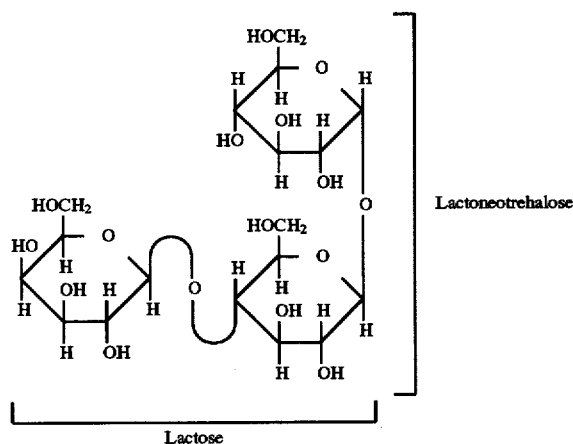

Structure of the crystal (lactoneotrehalose)

Based on the above structure, the substance according to the invention is named as lactoneotrehalose.

(13) Powder x-ray diffraction analysis The powder x-ray diffraction pattern of a crystalline lactoneotrehalose specimen was determined with "GEIGERFLEX RAD-IIB (CuKα ray)", a product of Rigaku Corp., Tokyo, Japan. The results were shown in FIG. 3. As evident from FIG. 3, the crystalline lactoneotrehalose exhibits predominant diffraction angles (2θ) of 12.8 °, 18.1°, 19.2°, 19.7° and 24.2° on powder x-ray diffraction analysis.

EXPERIMENT 2

Preparation and Physicochemical Properties of Neotrehalose

Experiment 2-1

Preparation of Neotrehalose

One part by weight of a crystalline lactoneotrehalose specimen obtained by the method in Experiment 1-1 was dissolved in 30 parts by weight of water while heating, adjusted to 40° C. and pH 4.5, added 10 units/g lactoneotrehalose of "LACTASE-LP", a β-galactosidase specimen commercialized by K.I Chemical Industry, Co., Ltd., Shizuoka, Japan, allowed to react for 20 hours, and heated at 100° C. for 10 minutes to inactivate the remaining enzyme. Similarly as in Experiment 1-1, the resultant solution containing about 66% neotrehalose and about 33% galactose, d.s.b., was decolored, deionized, purified, concentrated, and subjected to column chromatography using a strongly-acidic cation exchange resin, followed by the recovery of neotrehalose-rich fractions.

A part of the neotrehalose-rich fractions containing about 88% neotrehalose, d.s.b., was concentrated to give a concentration of 75%, and allowed to stand overnight at 20° C. to effect crystallization. The resultant crystal was added as seed to a solution having a concentration of 70% which had been prepared by concentrating the neotrehalose-rich fractions, and allowed to effect crystallization under gentle stirring conditions. The resultant massecuite was separated, and the formed crystal was washed by spraying thereunto a small amount of water to obtain a high-purity crystal which was then dissolved in water and recrystallized similarly as above to obtain about 0.15 parts by weight of a high-purity crystalline neotrehalose, purity of 99.8% or higher.

Experiment 2-2

Physicochemical Properties of Neotrehalose

The physicochemical properties of neotrehalose were studied with a high-purity crystalline neotrehalose specimen prepared by the method in Experiment 2-1.

Figure 5:
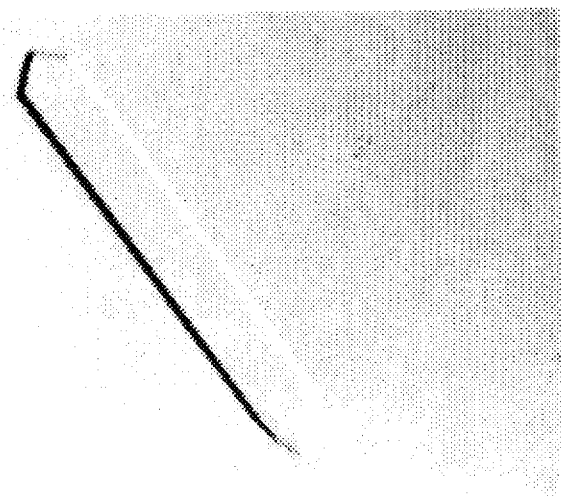
FIG. 5 shows a microscopic photograph (×125) of a crystalline neotrehalose specimen.
Figure 4:
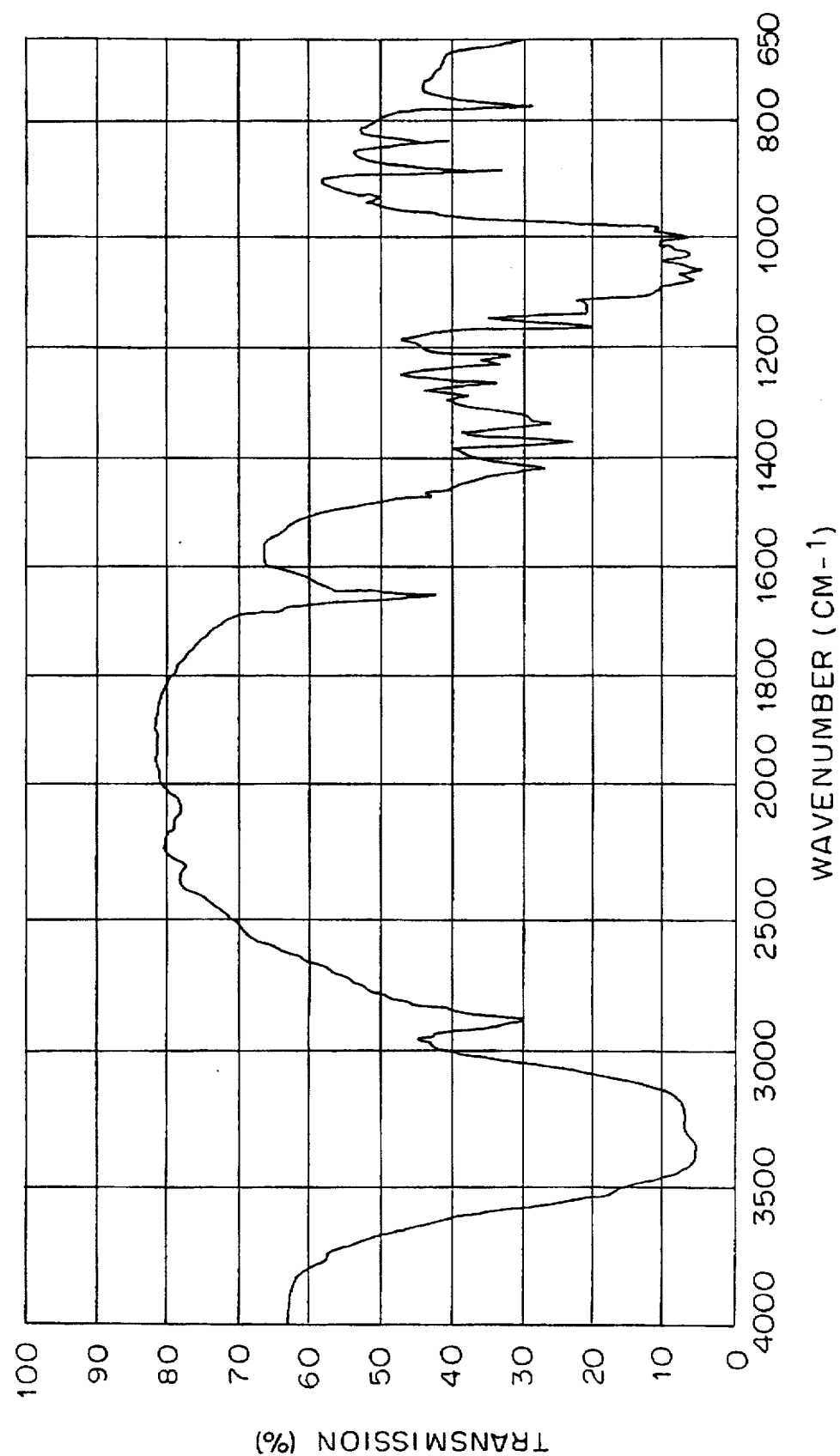
FIG. 4 shows an infrared absorption spectrum of a crystalline neotrehalose specimen.

(1) Elemental analysis Found; C=40.0%, H=6.7%, O=53.3% Calculated; C=40.00%, H=6.71%, O=53.29% (for chemical formula $C_{12}H_{22}O_{11}.H_2O$)
  (2) Molecular weight 360.3
  (3) Melting point 144.5°–145° C.
  (4) Specific rotation $[α]_D^{20}$=+93.9° (c=2.0, $H_2O$)
  (5) uv-Absorption spectrum Exhibiting no characteristic uv-absorption when tested in water.
  (6) Infrared absorption spectrum Two mg of the crystal and 200 mg of dried KBr were mixed by stirring to obtain about 0.6 mm thick transparent tablet, and the infrared spectrum of the crystal was determined therewith. The result was shown in FIG. 4.
  (7) Solubility Fifty-five g of the crystal in the form of anhydride dissolves in 100 g water at 25° C.
  (8) Physical properties and color Colorless and transparent crystal. Pulverized crystal has a favorable taste and about ⅓ sweetening power of sucrose and exhibits a white appearance, but exhibits no odor. Free of hygroscopicity and deliquescence. The Karl Fischer's method revealed that the moisture content of crystals predried in vacuo at 60° C. for 16 hours is less than 5.2%, and this showed that the crystal was a monohydrate crystal. FIG. 5 shows a microscopic photograph of a crystal obtained by crystallization in an aqueous solution. An aqueous solution of the crystal shows neutral or slight acidity.

(9) Solubility in solvents Readily soluble in water, 0.1N sodium hydroxide, and 0.1N hydrochloric acid; scarcely soluble in methanol and ethanol; and insoluble in chloroform and ethyl acetate.

(10) Coloring reaction Turning green on the anthrone-sulfuric acid reaction. Negative to both the Fehling'reaction and the iodine coloration reaction.

(11) Structure
  (a) Hydrolysis with 1N-sulfuric acid gives 2 moles of D-glucose per one mole of the crystal.
  (b) Gas chromatographic analysis on saccharides obtained by acetylating the crystal with methylhexitol revealed that the crystal consisted of 1,5-di-O-acetyl-2,3,4,6-tetra-O-methylglucitol, and this confirmed that the glucose molecules in the crystal were bound at the C-1 position of each glucose molecule.
  (c) Infrared absorption spectrum of the crystal gives the absorption near at 880 cm$^{-1}$ inherent to β-D-glucopyranosyl bond, and the absorption near at 840 cm$^{-1}$ inherent to α-D-glucopyranosyl bond.
  (d) When subjected to the action of α-glucosidase, D-glucose is formed, but not hydrolyzed by trehalase.

Based on the above results, the chemical structure of the crystal can be shown as follows:

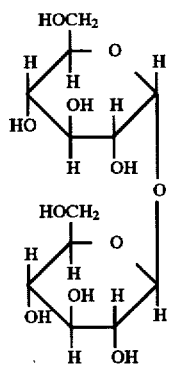

Structure of the crystal (neotrehalose)

(12) Powder x-ray diffraction analysis The powder x-ray diffraction pattern of a crystalline neotrehalose specimen was determined with "GEIGERFLEX RAD-IIB (CuKα ray)", a product of Rigaku Corp., Tokyo, Japan. The results were shown in FIG. 6.

Figure 6:
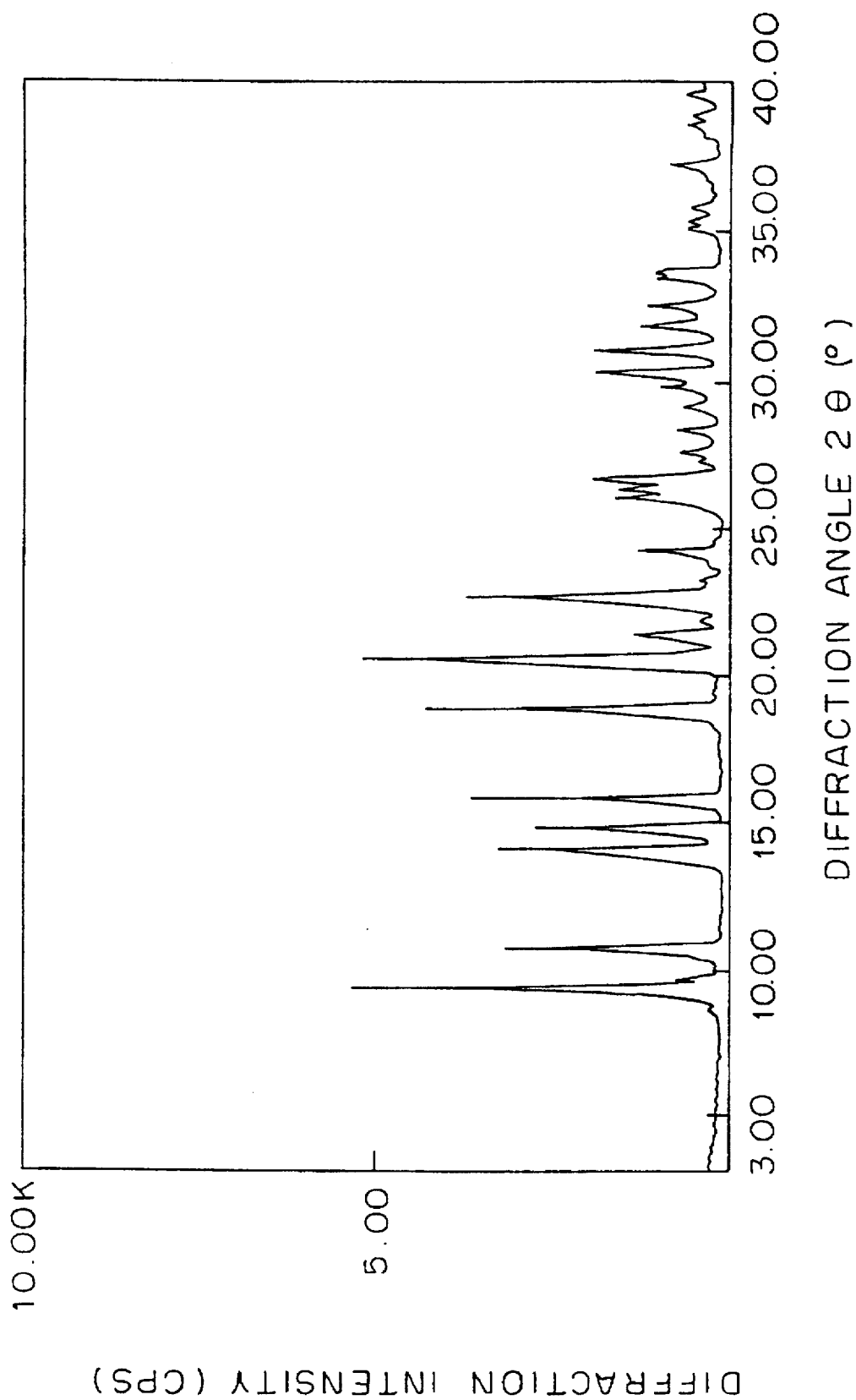
FIG. 6 shows a powder x-ray diffraction pattern of a crystalline neotrehalose specimen.

As evident from FIG. 6, the crystalline neotrehalose exhibits predominant diffraction angles (2θ) of 9.3°, 15.8°, 18.9°, 20.6° and 22.7° C. on powder x-ray diffraction analysis.

Experiment 2-3
Digestion Test

In accordance with the method described in H. Atsuji et al., *Journal of Clinical Nutrition*, Vol.41, Vol.2, pp.200–208 (1972), the load test by orally-administering to healthy volunteers a crystalline neotrehalose specimen prepared by the method in Experiment 2-1 was done, and their blood was sampled at prescribed time intervals and subjected to the measurements of the blood sugar and insulin levels. As control, glucose was used.

As a result, neotrehalose behaved similarly as to glucose, and the maximum levels of blood sugar and insulin were apparent about 0.5–1 hour after the administration.

This confirmed that neotrehalose was readily digested, absorbed, metabolized and utilized into energy.

Experiment 2-4
Acute Toxicity

A crystalline neotrehalose specimen, prepared by the method in Experiment 2-1, was orally administered to 7 week-old dd mice for acute toxicity test. As a result, no animal death was noted with the administration of up to 5 g of the specimen and higher dose was difficult to do.

Therefore, the toxicity of the tested substance appears to be extremely low.

Examples for reference and Examples A will illustrate the preparations of lactoneotrehalose and the neotrehalose according to the present invention; and Examples B, the orally-administrable products according to the present invention.

EXAMPLE FOR REFERENCE 1

One part by weight of lactose and 2 parts by weight of "PINE-DEX #4", a dextrin product (DE 18) commercialized by Matsutani Chemical Ind., Co., Ltd., Kyoto, Japan, were dissolved in 3.7 parts by weight of water while heating, and the solution was heated to 60° C., adjusted to pH 5.6, added with 300 units/g dextrin of a cyclomaltodextrin glucanotransferase specimen commercialized by Hayashibara Biochemical Laboratories, Inc., Okayama, Japan, allowed to react for 20 hours, and heated to inactivate the remaining enzyme. The resultant mixture was in an usual manner decolored with activated charcoal, deionized, purified and concentrated into a syrup having a concentration of 75% in the yield of about 92%, d.s.b.

The product containing about 15% lactoneotrehalose, d.s.b., exhibits a moderate sweetness, appropriate viscosity and moisture-retaining ability, and these render the product very useful in orally-administrable products.

EXAMPLE FOR REFERENCE 2

One part by weight of lactose and 1.5 parts by weight of α-cyclodextrin were dissolved in 4 parts by weight of water while heating, and the solution was first heated to 65° C., adjusted to pH 5.6, added with 200 units/g dextrin of fresh cyclomaltodextrin glucanotransferase as used in Example for reference 1, and allowed to react for 24 hours. Thereafter, the resultant solution was heated to inactivate the remaining enzyme, cooled to 55° C., adjusted to pH 5.6, added with 10 units/g dextrin of "β-amylase #1500", a β-amylase specimen commercialized by Nagase Biochemicals Ltd., Kyoto, Japan, and allowed to react for 16 hours. After completion of the reaction, the mixture was heated to inactivate the remaining enzyme. Similarly as in Example for reference 1, the resultant mixture was purified and concentrated into a syrup having a concentration of 75% in the yield of about 93%, d.s.b.

The product containing about 25% lactoneotrehalose, d.s.b., exhibits a moderate sweetness, appropriate viscosity and moisture-retaining ability, and these render the product very useful in orally-administrable products similarly as the product in Example for reference 1.

EXAMPLE FOR REFERENCE 3

To a starch slurry, concentration of 20%, was added 0.15% of "Termamyl® 60L", an α-amylase specimen commercialized by Novo Industri Japan, Ltd., Tokyo, Japan, against starch, d.s.b., and the mixture was heated to a temperature in the range of 95°–100° C. to effect liquefaction, and further heated to inactivate the remaining enzyme to obtain a liquefied solution (DE 3) which was then added with lactose equivalent to the amount of amylaceous substance contained in the liquefied solution, d.s.b. The resultant mixture was heated to 55° C., adjusted to pH 5.3, added with 50 units/g starch of an isoamylase specimen commercialized by Hayashibara Biochemical Laboratories Inc., Okayama, Japan, together with 300 units/g starch of the same cyclomaltodextrin glucanotransferase as used in Example for reference 1, and allowed to react for 24 hours. Thereafter, the mixture thus obtained was heated to inactivate the remaining enzyme, diluted with water to give a concentration of about 25%, heated to 55° C., adjusted to pH 5.3, added with 15 units/g dextrin of glucoamylase, allowed to react for 16 hours, and further heated to inactivate the remaining enzyme. Similarly as in Example for reference 1, the solution thus obtained was purified and concentrated into a syrup having a concentration of 75% in the yield of about 90%, d.s.b.

The product containing about 34% lactoneotrehalose, d.s.b., exhibits a moderate sweetness, appropriate viscosity and moisture-retaining ability, and these render the product very useful in orally-administrable products similarly as the product in Example for reference 1.

EXAMPLE FOR REFERENCE 4

To a liquefied solution (DE 3) prepared by the method in Example for reference 3 was dissolved 2-fold amounts of lactose against the amylaceous substance in the liquefied solution, d.s.b. The mixture was heated to 60° C., adjusted to pH 5.6, added with 100 units/g dextrin of cyclomaltodextrin glucanotransferase, allowed to react for 48 hours, and heated to inactivate the remaining enzyme. Similarly as in Example for reference 3, the resultant mixture was added with glucoamylase to effect an enzymatic reaction and heated to inactivate the remaining enzyme. Similarly as in example for reference 1, the resultant solution was purified and concentrated into a syrup, concentration of 75%, which was then transferred to a crystallizer to effect crystallization by the addition of a small amount of crystalline lactose. Thereafter, the mixture was centrifuged to remove crystalline lactoneotrehalose and the resultant solution was concentrated into a syrup having a concentration of 75% in the yield of about 70%, d.s.b.

The product containing about 35% lactoneotrehalose, d.s.b., exhibits a moderate sweetness, appropriate viscosity and moisture-retaining ability, and these render the product very useful in orally-administrable products similarly as the product in Example for reference 1.

EXAMPLE A-1

A solution containing about 15% lactoneotrehalose, d.s.b., prepared by the method in Example for reference 1, was concentrated to give a concentration of 45%, and the resultant was heated to 40° C., adjusted to pH 4.5, added with 15 units/g lactoneotrehalose of "LACTASE-LP", a β-galactosidase specimen, allowed to react for 24 hours, and heated to inactivate the remaining enzyme.

The resultant solution was decolored in an usual manner with activated charcoal, deionized with ion-exchange resins ($H^+$ and $OH^-$ form), purified and concentrated into a syrup having a concentration of 75% in the yield of about 92%, d.s.b.

The product containing about 10% neotrehalose, d.s.b., exhibits a rich sweetness, appropriate viscosity and moisture-retaining ability, and these render the product very useful in orally-administrable products.

EXAMPLE A-2

A solution containing about 25% lactoneotrehalose, d.s.b., prepared by the method in Example for reference 2, was concentrated to give a concentration of about 40%, and the resultant was heated to 45° C., adjusted to pH 7.2, added with 10 units/g lactoneotrehalose of "LACTOZYM 3000L", a β-galactosidase specimen commercialized by Novo Industri Japan, Ltd., Tokyo, Japan, allowed to react for 20 hours, and heated to inactivate the remaining enzyme.

Similarly as in Example A-1, the resultant solution was purified and concentrated into a syrup having a concentration of 75% in the yield of about 93%, d.s.b.

Similarly as the product in Example A-1, the product containing about 16% neotrehalose, d.s.b., exhibits a rich sweetness, appropriate viscosity and moisture-retaining ability, and these render the product very useful in orally-administrable products.

EXAMPLE A-3

A solution containing about 34% lactoneotrehalose, d.s.b., prepared by the method in Example for reference 3, was concentrated to give a concentration of about 35%, and the resultant solution was heated to 40° C., adjusted to pH 4.5, added with β-galactosidase similarly as in Example A-1, allowed to react, and heated to inactivate the remaining enzyme.

Similarly as in Example A-1, the solution thus obtained was purified and concentrated into a syrup having a concentration of 75% in the yield of about 94%, d.s.b.

Similarly as the product in Example A-1, the product containing about 22% neotrehalose, d.s.b., exhibits a rich sweetness, appropriate viscosity and moisture-retaining ability, and these render the product very useful in orally-administrable products.

EXAMPLE A-4

A solution containing about 35% lactoneotrehalose, d.s.b., prepared by the method in Example for reference 4, was concentrated to give a concentration of about 35%, and the resultant solution was heated to 45° C., adjusted to pH 7.2, added with β-galactosidase similarly as in Example A-2, allowed to react, and heated to inactivate the remaining enzyme.

Similarly as in Example A-1, the solution thus obtained was purified and concentrated into a syrup having a concentration of 75% in the yield of about 94%, d.s.b.

Similarly as the product in Example A-1, the product containing about 22% neotrehalose, d.s.b., exhibits a rich sweetness, appropriate viscosity and moisture-retaining ability, and these render the product very useful in orally-administrable products.

EXAMPLE A-5

A solution containing about 66% neotrehalose, d.s.b., prepared by using the reaction- and purification-methods in Experiment 2-1, as a material saccharide solution, was concentrated to give a concentration of about 45%. In order to increase the neotrehalose content in the resultant solution, which was subjected to column chromatography similarly as the method in Experiment 1-1 except that "DOWEX 50W×4 ($Ca^{++}$-form)", a strongly-acidic cation exchange resin commercialized by Dow Chemical Company, Midland, Mich. USA, was used as a resin for fractionation to obtain a neotrehalose-rich fraction containing about 85% neotrehalose, d.s.b. The fraction was concentrated to give a concentration of about 83%, and the resultant solution was transferred to a crystallizer and admixed with an about one % seed. The mixture was transferred to a tray and allowed to stand at 20° C. for 4 days to effect crystalization and solidification. Thereafter, the resultant solid was pulverized with a cutting-type pulverizer and dried to obtain a crystalline neotrehalose powder containing molasses in the yield of about 70%, d.s.b.

The product is readily handleable and substantially free of hygroscopicity, and these render the product very useful in orally-administrable products as a sweetener, stabilizer, taste-improving agent and quality-improving agent.

EXAMPLE A-6

In order to higher the neotrehalose content in an about 22% high-neotrehalose content solution, d.s.b., prepared by using the reaction- and purification-methods in Example A-5, as a material saccharide solution, was subjected to column chromatography according to the method in Example A-5 to obtain a neotrehalose-rich fraction containing about 75% neotrehalose, d.s.b. The fraction was concentrated to give a concentration of about 77%, transferred to a crystallizer, added with an about 2% seed, and gradually cooled to obtain a massecuite having a crystallization degree of about 35%, which was then sprayed through a nozzle equipped at the top of a spraying tower with a pressure of 150 kg/cm². Simultaneously, 85° C. air was passed from the top of the tower towards a net conveyer, provided at the bottom of the tower, to collect the pulverized product on the net conveyer and also to gradually carry the resultant crystalline powder out of the tower while passing a stream of 45° C. air upwards through the net conveyer. The crystalline powder was then placed in an ageing tower and aged for 10 hours to effect crystallization and dehydration. Thus, a crystalline neotrehalose powder containing molasses was obtained in the yield of about 25%, d.s.b.

The product is readily handleable and substantially free of hygroscopicity, and these render the product very useful in orally-administrable products as a sweetener, stabilizer, taste-improving agent and quality-improving agent.

EXAMPLE A-7

An about 66% high-neotrehalose content solution, d.s.b., prepared by using the reaction- and purification-methods in Experiment 2-1, as a material saccharide solution, was concentrated to give a concentration of about 75%. In order to higher the neotrehalose content in the resultant solution, which was transferred to a crystallizer, added with an about one % of a powdery seed, and gradually cooled to effect crystallization under stirring conditions. Thereafter, the resultant mixture was subjected to separation with a basket-type centrifuge to obtain a crystal which was then washed by spraying thereto a small amount of water. Thus, a high-purity crystalline neotrehalose was obtained in the yield of about 35%, d.s.b.

The product exhibits the same physicochemical properties as the product in Experiment 2-2, and these render the product very useful in orally-administrable products as a sweetener, stabilizer, taste-improving agent and quality-improving agent. The product can be also used in industrial reagents and chemical materials.

EXAMPLE B-1

Sweetner

One part by weight of a crystalline neotrehalose obtained by the method in Example A-6 was mixed to homogeneity with 0.05 parts by weight of "α-G sweet", an α-glycosyl stevioside product commercialized by Toyo Sugar Refining Co., Ltd., Tokyo, Japan, and the mixture was subjected to a granulator to obtain a sweetener in the form of granule.

Since the sweetener has a satisfiable quality of sweetness and an about 2-fold higher sweetening power than sucrose, the calorific value of the sweetener lowers to about half of that of sucrose per sweetening power.

The sweetener can be advantageously used as a low-caloric sweetener in low-caloric foods and beverages for overweight persons and diabetics who are restricted to a special diet.

Since caries-inducing microorganisms are less likely to form acids and insoluble glucans when administered the sweetener, the sweetener can be favorably used as a sweetener in caries-preventing foods and beverages.

EXAMPLE B-2

Hard Candy

One hundred parts by weight of a 55% sucrose solution and 30 parts by weight of a syrup containing neotrehalose, obtained by the method in Example A-2, were mixed by heating. Thereafter, the mixture was concentrated by heating in vacuo until the moisture content decreased to lower than 2%, and further admixed with one part by weight of citric acid and adequate amounts of a coloring agent and lemon flavor. The resultant mixture was formed into the captioned product in a usual manner.

The product is a high-quality hard candy having a satisfiable taste and biting property, wherein the crystallization of sucrose is prevented.

EXAMPLE B-3

Strawberry Jam

One hundred and fifty parts by weight of strawberry, 60 parts by weight of sucrose, 20 parts by weight of maltose, 40 parts by weight of a syrup containing neotrehalose obtained by the method in Example A-4, 5 parts by weight of pectin and one part by weight of citric acid were boiled up in a vessel and the mixture was bottled into the captioned product.

The product is a favorable strawberry jam having a satisfiable flavor and color.

EXAMPLE B-4

Lactic Acid Beverage

Ten parts by weight of defatted milk was sterilized by heating at 80° C. for 20 minutes, cooled to 40° C., added with 0.3 parts by weight of a starter, and fermented at about 37° C. for 10 hours. Thereafter, the mixture was homogenized and added with 4 parts by weight of a crystalline neotrehalose powder obtained by the method in Example A-5, one part by weight of sucrose, and 2 parts by weight of an isomerized syrup. The resultant mixture was sterilized at 70° C., cooled, added with an adequate amount of a flavoring agent, and bottled to obtain the captioned product.

The product is a high-quality lactic acid beverage having a sour taste which is satisfactorily harmonized with flavor and sweetness.

EXAMPLE B-5

Sweetened Condensed Milk

To 100 parts by weight of milk was dissolved one part by weight of sucrose and 3 parts by weight of a syrup containing neotrehalose obtained by the method in Example A-1, and the mixture was sterilized by heating with a plate heater, concentrated to give a concentration of about 70%, and aseptically canned to obtain the captioned product.

The product has a moderate sweetness and a satisfiable flavor, and these render the product very useful as seasoning in foods for baby and infant, fruit, coffee, cocoa and tea.

EXAMPLE B-6

Fruit-Juice Powder

Thirty-three parts by weight of pulverized orange juice prepared by spray-drying was stirred and mixed to homogeneity with 50 parts by weight of a crystalline neotrehalose obtained by the method in Example A-7, 10 parts by weight of sucrose, 0.65 parts by weight of anhydrous citric acid, 0.1 part by weight malic acid, 0.1 part by weight of L-ascorbic acid, 0.1 part by weight of sodium citrate, 0.5 parts by weight of pullulan, and an adequate amount of a powdery flavoring agent. The mixture was pulverized, and the resultant powder was fed to a fluidized-bed granulator and granulated at an inlet temperature of 40° C. and an air-flow-rate of 150 m³/min for 30 minutes while spraying the content with a high-neotrehalose content solution, obtained by the method in Example A-5, as a binder. Thereafter, the resultant was weighed and packaged to obtain the captioned product.

The product is a fruit-juice powder having an orange juice content of about 30%. The product is free of an unfavorable taste and odor, and stable over a relatively long period of time without being solidified by absorbing moisture.

EXAMPLE B-7

Chocolate

Forty parts by weight of cacao paste, 10 parts by weight of cacao butter, and 50 parts by weight of a crystalline neotrehalose obtained by the method in Example A-7 were mixed, and the mixture was fed to a refiner to reduce the particle size, transferred to a conche, and kneaded therein at 50° C. for 2 days. In the kneading step, 0.5 parts by weight of lecithin was added and dispersed to homogeneity. Thereafter, the content was adjusted to 31° C. with a thermoregulator, and placed in a mold immediately before the solidification of the butter, deaerated with a vibrator, and solidified by passing it through a 10° C. cooling tunnel over a period of 20 minutes. The content was removed from the mold and packaged to obtain the captioned product.

The product with an excellent color, gloss and texture exhibits no hygroscopicity and smoothly melts in the mouth to exhibit a moderate sweetness and smooth flavor.

EXAMPLE B-8

Chewing Gum

Three parts by weight of a gum base was melted by heating until it softened, and admixed with 4 parts by weight of sucrose, 3 parts by weight of a crystalline neotrehalose powder obtained by the method in Example A-6, and adequate amounts of a flavoring agent and coloring agent. The mixture was kneaded with a roll in an usual manner, formed and packaged to obtain the captioned product.

The product is a favorable chewing gum having a satisfiable texture and flavor.

EXAMPLE B-9

Custard Cream

One hundred parts by weight of corn starch, 100 parts by weight of a syrup containing neotrehalose obtained by the method in Example A-4, 80 parts by weight of maltose, 20 parts by weight of sucrose, and one part by weight of salt were mixed to homogeneity. The mixture was admixed with 280 parts by weight of eggs and gradually added with 1,000 parts by weight of a boiling milk. The resultant mixture was heated while stirring, and the heating was stopped when the whole content turned semi-transparent. Thereafter, the resultant product was cooled and added with an adequate amount of vanilla flavor, and the mixture was weighed, filled up and packaged to obtain the captioned product.

The product has a smooth gloss, moderate sweetness and satisfiable taste.

EXAMPLE B-10

"Uiro-no-moto" (Premix of Sweet Rice Jelly)

An uiro-no-moto was prepared by mixing to homogeneity 90 parts by weight of rice powder, 20 parts by weight of corn starch, 120 parts by weight of a crystalline neotrehalose powder obtained by the method in Example A-5, and 4 parts by weight of pullulan. The mixture was kneaded with adequate amounts of "matcha" (powdered green tea) and water, and the resultant mixture was placed in a vessel and steamed up over a period of 60 minutes to obtain an uiro containing matcha.

The product has a satisfiable gloss, biting-property and flavor. The shelf-life of the product is relatively long because the retrogradation of starch in the product is inhibited.

EXAMPLE B-11

Interferon Tablet

A natural human interferon-α specimen produced by Hayashibara Biochemical Laboratories Inc., Okayama, Japan, and commercialized by Cosmo Bio Co., Ltd., Tokyo, Japan, was subjected in an usual manner to column chromatography using an immobilized anti-human interferon-α antibody to adsorb thereto the human natural interferon-α contained in the specimen, as well as to remove calf serum-albumin as a stabilizer by passing it though the column. Thereafter, the pH in the column was changed, and the natural human interferon-α was eluted from the column with a physiological saline containing 5% of a crystalline neotrehalose specimen obtained by the method in Example A-7. The resultant solution was membrane-filtered, and the filtrate was dehydrated and pulverized by the addition of 20-fold volumes of "FINETOSE®", an anhydrous crystalline maltose powder commercialized by Hayashibara Shoji Inc., Okayama, Japan, and the resultant powder was tabletted with a tabletting machine to obtain the captioned product containing about 150 units/tablet of natural human interferon-α, about 200 mg each.

In use, the product is orally-administered to the adult in an amount of 1–10 tablets/day/adult as a sublingual tablet, and can be advantageously used in the treatment of viral diseases, allergic diseases, rheumatism, diabetics and malignant tumors. More particularly, the product can be advantageously used as a therapeutic agent for patients suffering from acquired immune deficiency syndrome (AIDS) and hepatitis, the number of which has been extremely increased recently.

Since neotrehalose and maltose act as stabilizer, the activity of the product is retained for a relatively long period of time even when allowed to stand at ambient temperature.

EXAMPLE B-12

Sugar-Coated Tablet

A plain tablet (150mg in weight) as a core tablet was coated with the first sugar-coating composition consisting of 40 parts by weight of a crystalline neotrehalose specimen obtained by the method in Example A-7, 2 parts by weight of pullulan (average molecular weight of 200,000), 30 parts by weight of water, 25 parts by weight of talc and 3 parts by weight of titanium oxide until the tablet weighed about 230 mg. Thereafter, the resultant tablet was first coated with the second sugar-coating composition consisting of 65 parts by weight of the same crystalline neotrehalose as used in the above, one part by weight of pullulan (average molecular weight of 200,000) and 34 parts by weight of water, then coated with a wax solution to impart a gloss. Thus, the captioned product having a gloss and satisfiable appearance was obtained.

The handleability in the sugar-coating step for the product is satisfactory, and the product has a satisfiable shock-resistance and retains its quality at a relatively high-level over a relatively long period of time.

[Effect of the Invention]

As described above, the present neotrehalose prepared by allowing β-galactosidase to act on lactoneotrehalose is obtained in a relatively high-yield: The separation- and purification-processes of the neotrehalose are facilitated. The neotrehalose is a non-reducing oligosaccharide having a satisfiable stability and a rich- and high-quality-sweetness. The neotrehalose is metabolized and utilized as energy source when orally administered. The neotrehalose in the form of crystal has a satisfiable handleability because it is readily soluble in water and substantially free of hygroscopicity.

The neotrehalose has merits, for example, a satisfiable chemical-stability, osmosis-pressure controlling ability, activating ability, gloss-imparting ability, moisture-retaining ability, viscosity-imparting ability, decreased fermentability, and crystallization-preventing ability for other saccharides. These render neotrehalose very useful in the preparations of orally-administrable products.

Accordingly, the establishment of the present preparation of neotrehalose and its uses have a great significance in the fields of food-, cosmetic- and pharmaceutical-industries.

While there has been described what is at present considered to be the preferred embodiments of the invention, it will be understood that various modifications may be made therein, and it is intended to cover in the appended claims all such modifications as fall within the true spirit and scope of the invention.

What is claimed is:

1. A process for preparing an orally-administrable composition comprising neotrehalose and an orally-administrable carrier, which comprises:
   (a) treating a solution containing lactoneotrehalose of the formula O-β-D-galactopyranosyl (1-4)-O-β-D-glycopyranosyl α-D-glucopyranoside with β-D-galactosidase (EC 3.2.1.23) to form neotrehalose;
   (b) recovering the resulting neotrehalose; and
   (c) incorporating the neotrehalose into an orally-administrable carrier.

2. The process according to claim 1 wherein said orally-administrable carrier is selected from the group consisting of foods, cigarettes, animal feed and pharmaceuticals.

3. The process according to claim 1 wherein step (c) includes a step of incorporating at least one additional sweetener into said orally-administrable carrier.

4. The process according to claim 1 wherein said neotrehalose is formulated with at least one filler selected from the group consisting of dextrin, starch and lactose.

5. A process for preparing a cosmetic comprising neotrehalose and a cosmetically-acceptable carrier, which comprises:
   (a) treating a solution containing lactoneotrehalose of the formula O-β-D-galactopyranosyl(1→4)-O-β-D-glucopyranosyl α-D-glucopyranoside with β-D-galactosidase (EC 3.2.1.23) to form neotrehalose;
   (b) recovering the resulting neotrehalose; and
   (c) incorporating the neotrehalose into a cosmetically-acceptable carrier.

6. The process according to claim 5 wherein the cosmetically-acceptable carrier is selected from the group consisting of dentifrices, lipstick, lip cream, oral rinses, and gargles.

7. A process for preparing a pharmaceutical composition comprising neotrehalose and a pharmaceutically-effective ingredient which comprises:
   (a) treating a solution containing lactoneotrehalose of the formula O-β-D-galactopyranosyl (1→4)-O-β-D-glucopyranosyl α-D-glucopyranoside with β-D-galactosidase (EC 3.2.1.23) to form neotrehalose;
   (b) recovering the resulting neotrehalose; and
   (c) incorporating the neotrehalose into a composition comprising a pharmaceutically effective ingredient.

8. The process according to claim 7 wherein step (c) includes a step of incorporating a pharmaceutically-acceptable carrier into said composition comprising a pharmaceutically effective ingredient.

9. A process for preparing an orally-administrable product comprising neotrehalose and an orally-administrable carrier, which comprises:
   (a) treating a solution containing lactotrehalose of the formula O-β-D-galactopyranosyl (1→4)-O-β-D-glucopyranosyl α-D-glucopyranoside with β-D-galactosidase (EC 3.2.1.23) to form neotrehalose;
   (b) purifying and concentrating the resultant solution into a supersaturated solution of neotrehalose to crystallize neotrehalose;
   (c) recovering the resultant crystalline neotrehalose; and
   (d) incorporating the crystalline neotrehalose into an orally-administrable carrier.

10. The process according to claim 9 wherein said orally-administrable carrier is selected from the group consisting of foods, cigarettes, animal feeds, and pharmaceuticals.

11. The process according to claim 9 wherein step (d) includes a step of incorporating at least one additional sweetener into said orally-administrable carrier.

12. The process according to claim 9 wherein step (d) includes a step of incorporating at least one filler selected from the group consisting of dextrin, starch and lactose into said orally-administrable carrier.

13. A process for preparing a cosmetic composition comprising neotrehalose and a cosmetically-acceptable carrier which comprises:
   (a) treating a solution containing lactoneotrehalose of the formula O-β-D-galactopyranosyl (1→4)-O-β-D-glucopyranosyl α-D-glucopyranoside with β-D-galactosidase (EC 3.2.1.23) to form neotrehalose;
   (b) recovering the resulting neotrehalose; and
   (c) incorporating the neotrehalose into a cosmetically-acceptable carrier.

14. The process according to claim 13 wherein said cosmetically-acceptable carrier is selected from the group consisting of dentifrices, lipstick, lip cream, oral rinses, and gargles.

* * * * *